United States Patent
Kang et al.

(10) Patent No.: US 12,419,842 B2
(45) Date of Patent: Sep. 23, 2025

(54) CONTROLLED-RELEASE FORMULATION FOR HEARING LOSS AND PREPARATION METHOD THEREFOR

(71) Applicants: MNH BIO CO., LTD., Gyeonggi-do (KR); SEOUL NATIONAL UNIVERSITY HOSPITAL, Seoul (KR)

(72) Inventors: Dae-Jung Kang, Gyeonggi-do (KR); Gwangmin An, Gyeonggi-do (KR); Myung-Whan Suh, Seoul (KR); Hui Li, Seoul (KR); Yu-Jung Hwang, Seoul (KR)

(73) Assignees: MNH BIO CO., LTD, Gyeonggi-Do (KR); SEOUL NATIONAL UNIVERSITY HOSPITAL, Seoul (KR)

( * ) Notice: Subject to any disclaimer, the term of this patent is extended or adjusted under 35 U.S.C. 154(b) by 534 days.

(21) Appl. No.: 17/797,249

(22) PCT Filed: Jan. 29, 2021

(86) PCT No.: PCT/KR2021/001248
§ 371 (c)(1),
(2) Date: Aug. 3, 2022

(87) PCT Pub. No.: WO2021/157968
PCT Pub. Date: Aug. 12, 2021

(65) Prior Publication Data
US 2023/0066553 A1 Mar. 2, 2023

(30) Foreign Application Priority Data
Feb. 3, 2020 (KR) .................. 10-2020-0012749

(51) Int. Cl.
*A61K 9/50* (2006.01)
*A61K 31/573* (2006.01)
*A61P 27/16* (2006.01)

(52) U.S. Cl.
CPC .......... *A61K 9/5036* (2013.01); *A61K 9/5089* (2013.01); *A61K 31/573* (2013.01); *A61P 27/16* (2018.01)

(58) Field of Classification Search
CPC ...................................... A61K 7/735
See application file for complete search history.

(56) References Cited

U.S. PATENT DOCUMENTS

| 6,197,326 B1 * | 3/2001 | Suzuki | A61K 9/5031 514/825 |
| 2010/0266512 A1 * | 10/2010 | Wenk | A61P 19/02 424/59 |
| 2015/0283080 A1 | 10/2015 | Modi | |

FOREIGN PATENT DOCUMENTS

| KR | 10-2010-0131391 A | 12/2010 |
| KR | 10-2012-0118559 A | 10/2012 |
| KR | 10-2015-0138540 A | 12/2015 |
| KR | 10-2018-0066779 A | 6/2018 |
| KR | 20180066779 A * | 6/2018 |

OTHER PUBLICATIONS

Kim et al., Biomaterials, 123, 2017, 155-171.*
International Search Report issued in corresponding International Application No. PCT/KR2021/001248 dated May 31, 2021, pp. 1-3, English Translation.

* cited by examiner

*Primary Examiner* — Kyle A Purdy
(74) *Attorney, Agent, or Firm* — George Likourezos; Carter, DeLuca & Farrell LLP

(57) ABSTRACT

The present invention relates to controlled release formulations for treating hearing loss and a method for preparing the same, and more particularly, to controlled release formulations for treating hearing loss prepared by dispersing a steroidal anti-inflammatory agent encapsulated in low molecular weight hyaluronic acid in an aqueous solution of high molecular weight hyaluronic acid and a method for preparing the same.

19 Claims, 7 Drawing Sheets

Basal turn

Middle turn

Apical turn

SURDEN01 + Magnevist, Lt
Low viscosity vehicle + Magnevist, Rt

CONTROLLED-RELEASE FORMULATION FOR HEARING LOSS AND PREPARATION METHOD THEREFOR

TECHNICAL FIELD

This application claims the priority of Korean Patent Application No. 10-2020-0012749, filed on Feb. 3, 2020, the entirety of which is a reference of the present application.

The present invention relates to controlled release formulations for treating hearing loss and a method for preparing the same, and more particularly, to drug-controlled release formulations for treating hearing loss prepared by dispersing a steroidal anti-inflammatory agent encapsulated in low molecular weight hyaluronic acid in an aqueous solution of high molecular weight hyaluronic acid and a method for preparing the same.

BACKGROUND ART

Hearing loss refers to a state in which hearing is impaired or lost from abnormality of hearing due to various causes. The ear consists of the outer ear (from the auricle to the tympanic membrane), the middle ear (from the tympanic membrane to the entrance to the cochlea), and the inner ear (inside the cochlea), and any problem occurring in any of these causes hearing loss. The hearing loss is divided into hearing loss due to disorders of the outer and the middle ear (conductive hearing loss) and hearing loss due to disorders of the inner ear and the auditory nervous system (sensorineural hearing loss). However, the hearing loss due to disorders of the outer and the middle ear is also restored when the disorders are treated, but the hearing loss due to disorders of the inner ear and the auditory nervous system is not restored in many cases even if the disorders are treated to cause great inconvenience to patients.

So far, the most standard method for treating hearing loss is systemic oral steroid administration. However, as a result of systemic steroid administration to healthy hearing loss patients, it was reported that one or more systemic side effects occurred in 33.0% of patients, and serious side effects such as hip fracture, toxic hepatitis, and death occurred in about 1% of the patients (Min K H and Suh M W, Kor J Audiol 2012).

Recently, in addition to the systemic high-dosage steroid administration, intratympanic steroid injection has been used for treating sudden hearing loss. Steroid is injected into the tympanic cavity through the tympanic membrane, and it is expected that the injected steroid will diffuse through the fenestra rotunda located between the tympanic cavity and the inner ear. However, since a drug injected into the tympanic cavity is released within several tens of minutes through the ear canal, the actual delivery time of the drug to the inner ear is shorter than 24 hours, which does not achieve a sufficient therapeutic effect.

Meanwhile, in Korean Patent Registration No. 10-1877894, there is disclosed a drug-controlled release formulation for treating hearing loss prepared by dispersing a steroidal anti-inflammatory agent encapsulated in biocompatible polymer-derived microspheres in a hyaluronic acid hydrogel. The drug-controlled release formulation for treating hearing loss exerted the effect of extending a release period of the steroidal anti-inflammatory agent, but there are inconvenience to use two types of chemically modified hyaluronic acid derivatives and essential for hydrogel production and a problem in that inflammation in the tympanic membrane is caused by a cross-linking agent to be necessarily involved for the production of hydrogels.

Therefore, there is a need for a formulation for treating hearing loss capable of reducing side effects caused by systemic steroid administration and delivering a drug in the tympanic cavity for a sufficient time for the treatment of hearing loss.

DISCLOSURE

Technical Problem

The present inventors conducted many studies to develop a formulation for treating hearing loss capable of reducing side effects caused by systemic steroid administration and delivering a drug in the tympanic cavity for a sufficient time for the treatment of hearing loss, and as a result, found that a composite formulation prepared by dispersing a steroidal anti-inflammatory agent encapsulated in low molecular weight hyaluronic acid in an aqueous solution of high molecular weight hyaluronic acid not only significantly increased a drug release period in the tympanic cavity, but also did not exhibit side effects of inflammatory response, and then completed the present invention.

Accordingly, an object of the present invention is to provide a drug-controlled release formulation in which a steroidal anti-inflammatory agent encapsulated in microspheres of hyaluronic acid or hyaluronic acid salt is dispersed in an aqueous solution of hyaluronic acid or hyaluronic acid salt having a molecular weight of greater than 5,000,000 g/mol.

Another object of the present invention is to provide a pharmaceutical composition for preventing or treating hearing loss comprising a steroidal anti-inflammatory agent encapsulated in microspheres of hyaluronic acid or hyaluronic acid salt as an active ingredient, wherein the microspheres are dispersed in an aqueous solution of hyaluronic acid or hyaluronic acid salt having a molecular weight of greater than 5,000,000 g/mol.

Another object of the present invention is to provide a pharmaceutical composition for preventing or treating hearing loss consisting of a steroidal anti-inflammatory agent encapsulated in microspheres of hyaluronic acid or hyaluronic acid salt, wherein the microspheres are dispersed in an aqueous solution of hyaluronic acid or hyaluronic acid salt having a molecular weight of greater than 5,000,000 g/mol.

Another object of the present invention is to provide a pharmaceutical composition for preventing or treating hearing loss essentially consisting of a steroidal anti-inflammatory agent encapsulated in microspheres of hyaluronic acid or hyaluronic acid salt, wherein the microspheres are dispersed in an aqueous solution of hyaluronic acid or hyaluronic acid salt having a molecular weight of greater than 5,000,000 g/mol.

Yet another object of the present invention is to provide a method for preparing the drug controlled release formulation comprising (a) encapsulating a steroidal anti-inflammatory agent in microspheres of hyaluronic acid or hyaluronic acid salt; (b) preparing an aqueous solution of hyaluronic acid or hyaluronic acid salt having a molecular weight of greater than 5,000,000 g/mol; and (c) dispersing the microspheres in the aqueous solution.

Still another object of the present invention is to provide the use of a steroidal anti-inflammatory agent encapsulated in microspheres of hyaluronic acid or hyaluronic acid salt to prepare a formulation for treating hearing loss, wherein the microspheres are dispersed in an aqueous solution of hyaluronic acid or hyaluronic acid salt having a molecular weight of greater than 5,000,000 g/mol.

Still another object of the present invention is to provide a method for treating hearing loss by administering an effective amount of a composition comprising a steroidal anti-inflammatory agent encapsulated in microspheres of hyaluronic acid or hyaluronic acid salt as an active ingredient to a subject in need thereof, wherein the microspheres are dispersed in an aqueous solution of hyaluronic acid or hyaluronic acid salt having a molecular weight of greater than 5,000,000 g/mol.

Technical Solution

In order to achieve the object of the present invention, the present invention provides a drug-controlled release formulation in which a steroidal anti-inflammatory agent encapsulated in microspheres of hyaluronic acid or hyaluronic acid salt is dispersed in an aqueous solution of hyaluronic acid or hyaluronic acid salt having a molecular weight of greater than 5,000,000 g/mol.

In order to achieve another object of the present invention, the present invention provides a pharmaceutical composition for preventing or treating hearing loss comprising a steroidal anti-inflammatory agent encapsulated in microspheres of hyaluronic acid or hyaluronic acid salt as an active ingredient, wherein the microspheres are dispersed in an aqueous solution of hyaluronic acid or hyaluronic acid salt having a molecular weight of greater than 5,000,000 g/mol.

In addition, the present invention provides a pharmaceutical composition for preventing or treating hearing loss consisting of a steroidal anti-inflammatory agent encapsulated in microspheres of hyaluronic acid or hyaluronic acid salt, wherein the microspheres are dispersed in an aqueous solution of hyaluronic acid or hyaluronic acid salt having a molecular weight of greater than 5,000,000 g/mol.

In addition, the present invention provides a pharmaceutical composition for preventing or treating hearing loss essentially consisting of a steroidal anti-inflammatory agent encapsulated in microspheres of hyaluronic acid or hyaluronic acid salt, wherein the microspheres are dispersed in an aqueous solution of hyaluronic acid or hyaluronic acid salt having a molecular weight of greater than 5,000,000 g/mol.

In order to achieve yet another object of the present invention, the present invention provides a method for preparing the drug controlled release formulation comprising (a) encapsulating a steroidal anti-inflammatory agent in microspheres of hyaluronic acid or hyaluronic acid salt; (b) preparing an aqueous solution of hyaluronic acid or hyaluronic acid salt having a molecular weight of greater than 5,000,000 g/mol; and (c) dispersing the microspheres in the aqueous solution.

In order to achieve still another object of the present invention, the present invention provides the use of a steroidal anti-inflammatory agent encapsulated in microspheres of hyaluronic acid or hyaluronic acid salt to prepare a formulation for treating hearing loss, wherein the microspheres are dispersed in an aqueous solution of hyaluronic acid or hyaluronic acid salt having a molecular weight of greater than 5,000,000 g/mol.

In order to achieve still another object of the present invention, the present invention provides a method for treating hearing loss by administering an effective amount of a composition comprising a steroidal anti-inflammatory agent encapsulated in microspheres of hyaluronic acid or hyaluronic acid salt as an active ingredient to a subject in need thereof, wherein the microspheres are dispersed in an aqueous solution of hyaluronic acid or hyaluronic acid salt having a molecular weight of greater than 5,000,000 g/mol.

Hereinafter, the present invention will be described in detail.

The present invention provides a drug-controlled release formulation in which a steroidal anti-inflammatory agent encapsulated in microspheres of hyaluronic acid or hyaluronic acid salt is dispersed in an aqueous solution of hyaluronic acid or hyaluronic acid salt having a molecular weight of greater than 5,000,000 g/mol.

In the present invention, the hyaluronic acid is a linear polymeric polysaccharide in which β-D-N-acetylglucosamine and β-D-glucuronic acid are alternately bound. It is known that the hyaluronic acid is not only distributed in connective tissues such as subcutaneous tissue and cartilage tissue of mammals, but also exists in the vitreous body of the eye or umbilical cord, and also exists in the capsule of streptococci or *bacillus*. Natural hyaluronic acid with excellent biocompatibility does not have cross-species specificity and tissue or organ specificity, and enhances skin's moisturizing power, maintains skin elasticity, and reduces damage to the lower layer of the skin when skin is damaged, and serves as a lubricant to facilitate the movement between cells of collage, a major component of the skin.

On the other hand, since natural hyaluronic acid is rapidly decomposed by hyaluronidase when injected into the body, in order to control this decomposition rate, hyaluronic acid derivatives that are crosslinked by various methods or modified in structure using chemicals are also prepared and used. However, in the present invention, the hyaluronic acid may be characterized to include only natural hyaluronic acid or a salt thereof that is not chemically modified.

In the present invention, the hyaluronic acid salt may be sodium hyaluronate, calcium hyaluronate, magnesium hyaluronate, zinc hyaluronate, cobalt hyaluronate, tetrabutylammonium hyaluronate, or a combination thereof, but is not limited thereto.

In the present invention, the "microspheres" are spherical fine particles having a diameter of less than several micrometers, and refer to particles used as a drug carrier due to excellent biocompatibility and biodegradability. In the present invention, the microspheres may be prepared using low molecular weight hyaluronic acid having a molecular weight of 100,000 g/mol or less, preferably hyaluronic acid having a molecular weight of 50,000 g/mol or less, more preferably hyaluronic acid having a molecular weight of 2,000 g/mol or less, most preferably hyaluronic acid having a molecular weight of 10,000 g/mol or less.

In the present invention, the "steroidal anti-inflammatory agent" refers to an agent having an anti-inflammatory role with steroid nuclei, for example, corticosteroids such as dexamethasone, prednisolone, methylprednisolone, betamethasone, hydrocortisone, or a combination thereof. Preferably, the steroidal anti-inflammatory agent may be dexamethasone.

In the present invention, the microspheres may be prepared through known methods such as phase separation method, spray drying method, solvent evaporation drying method, and low temperature solvent extraction method.

According to an embodiment of the present invention, the microspheres were prepared by adding a steroidal anti-inflammatory agent to an aqueous solution of low molecular weight hyaluronic acid, and then adding an electrolyte aqueous solution to the solution to induce complex formation between the hyaluronic acid and the electrolyte.

The drug-controlled release formulation of the present invention may be characterized in that the aforementioned hyaluronic acid microspheres are dispersed in an aqueous solution of ultra-high molecular weight hyaluronic acid or hyaluronic acid salt having a molecular weight of greater than 5,000,000 g/mol.

The ultra-high molecular weight hyaluronic acid or its salt is not chemically modified, for example, a natural ultra-high molecular weight hyaluronic acid that is not modified with a chemical functional group such as hyaluronic acid diaminobutane, hyaluronic acid succinimide, and the like.

The ultra-high molecular weight hyaluronic acid may have a molecular weight of greater than 5,000,000 g/mol, preferably greater than 5,100,000 g/mol, more preferably greater than 5,200,000 g/mol, even more preferably greater than 5,300,000 g/mol, most preferably greater than 5,400,000 g/mol.

The molecular weight upper limit of the ultra-high molecular weight hyaluronic acid is not particularly limited, and as high molecular weight hyaluronic acid naturally present in nature, it will be apparent to those skilled in the art that any ultra-high molecular weight hyaluronic acid having a molecular weight of greater than 5,000,000 g/mol is applied to the present invention to exhibit the same effect. The molecular weight upper limit of the ultra-high molecular weight hyaluronic acid may be preferably 10,000,000 g/mol, more preferably 9,000,000 g/mol, much more preferably 8,000,000 g/mol, most preferably 7,500,000 g/mol.

According to one embodiment of the present invention, the ultra-high molecular weight hyaluronic acid may be produced by a *Streptococcus* sp. UBC-U46 (Accession No. KCTC13556BP) strain. The hyaluronic acid produced by the microorganism may be prepared with reference to Korean Patent No. 10-2018-0130275, which is referred to in the present invention.

In the present invention, the concentration of the hyaluronic acid or hyaluronic acid salt aqueous solution may be appropriately adjusted by those skilled in the art in consideration of the release time of a steroidal anti-inflammatory agent to be controlled release, but may be an aqueous solution of hyaluronic acid of 1.0 to 10.0% (w/v), preferably 1.5 to 8% (w/v), more preferably 2.0 to 7% (w/v), much more preferably 2.5 to 6% (w/v), most preferably 3.0 to 5% (w/v).

The release rate and release period of the steroidal anti-inflammatory agent in the controlled release formulation of the present invention may be controlled by a concentration of the aqueous solution of ultra-high molecular weight hyaluronic acid and a molecular weight of the ultra-high molecular weight hyaluronic acid, and may be adjusted by those skilled in the art according to a target site to be treated, the severity of a disease to be treated, and the like.

In addition to ultra-high molecular weight hyaluronic acid and water, the aqueous solution of ultra-high molecular weight hyaluronic acid does not contain any material such as a crosslinking agent, a curing agent, a chemical modifier, fatty acids, a cationic polymer that forms a complex with hyaluronic acid, and the like.

The crosslinking agent is a compound that reacts with hyaluronic acid to form a three-dimensional network structure, and may be at least one compound selected from the group consisting of a polyvalent epoxy compound such as polyglycidyl ether, divinyl sulfone, formaldehyde, phosphorus oxychloride, a combination of a carbodiimide compound and amino acid ester, and a combination of a carbodiimide compound and a dihydrazide compound.

The chemical modifier is a compound that reacts with a carboxyl group, a hydroxyl group, or an acetamido group of hyaluronic acid to form a covalent bond, and may be at least one compound selected from the group consisting of a combination of acetic anhydride and concentrated sulfuric acid, a combination of trifluoroacetic anhydride and organic acid, and an alkyl iodine compound.

The cationic polymer forming the complex with the hyaluronic acid is a polymer that forms a complex through an ionic bond between a carboxyl group of hyaluronic acid and an amino group or imino group of the polymer compound, and may be at least one cationic polymer selected from the group consisting of chitosan, polylysine, polyvinylpyridine, polyethyleneimine and polydimethylaminoethyl methacrylate.

In the case of using a chemical crosslinking agent and/or curing agent to prepare a hyaluronic acid hydrogel, these chemicals remain inside the hyaluronic acid hydrogel or in an outer carrier to increase a possibility of inducing harmful reactions such as an inflammatory response. However, the drug-controlled release formulation of the present invention may exhibit physiological activity very safely after being injected into the body because no chemicals are added to the aqueous solution of ultra-high molecular weight hyaluronic acid.

In one embodiment of the present invention, the aqueous solution of ultra-high molecular weight hyaluronic acid may be characterized as natural hyaluronic acid in which crosslinking is not induced by any means such as radiation, heat, and the like.

According to an embodiment of the present invention, the drug-controlled release formulation of the present invention using an aqueous solution of ultra-high molecular weight hyaluronic acid as a dispersion did not induce any inflammatory response after administration into the tympanic cavity. However, in the case of a formulation using a hydrogel prepared by treating a hyaluronic acid derivative with a crosslinking agent as a dispersion, it was confirmed that the formulation induced a serious inflammatory response after administration into the tympanic cavity.

In the present invention, in the drug-controlled release formulation, the concentration at which the microspheres of hyaluronic acid or hyaluronic acid salt are dispersed in the aqueous solution of ultra-high molecular weight hyaluronic acid or hyaluronic acid salt may be properly adjusted by those skilled in the art according to a release period, a release concentration, or the like of the steroidal anti-inflammatory agent included in the microspheres. For example, the microspheres may be dispersed at a concentration of 0.1 to 5% (w/v), preferably 0.5 to 4% (w/v), more preferably 0.5 to 3% (w/v), much more preferably 0.5 to 2.5% (w/v), most preferably 1 to 2% (w/v).

In one embodiment of the present invention, the formulation may be a controlled release formulation so as to release an active drug at a target site for a predetermined period. The formulation may release the steroidal anti-inflammatory agent for a long period of 20 days or longer, 1 month or more, 40 days or longer, 2 months or more, 4 months or more, 6 months or more, 6 months to 12 months, or 12 months or more. In one embodiment, the release period may be adjusted according to a molecular weight of the ultra-high molecular weight hyaluronic acid or a concentration of its aqueous solution. The target site refers to a specific organ of a subject, and is not limited to eyes, nose, ears, heart, ventricle, atrium, intestinal tract, blood vessels, or joints. In one embodiment, the target site may be ears, and the ears may include the middle ear, the inner ear, the cochlea, the vestibular organ, the eustachian tube or the tympanic cavity.

The present invention provides a pharmaceutical composition for preventing or treating hearing loss comprising a steroidal anti-inflammatory agent encapsulated in microspheres of hyaluronic acid or hyaluronic acid salt as an active ingredient, wherein the microspheres are dispersed in an aqueous solution of hyaluronic acid or hyaluronic acid salt having a molecular weight of greater than 5,000,000 g/mol.

In the present invention, the hearing loss includes ototoxic hearing loss caused by presbycusis, anticancer drugs, antipyretics, analgesics, antibiotics, etc., noise-induced hearing loss caused by industrial noise, gun noise, explosion noise, etc., traumatic hearing loss such as Meniere's disease, hearing loss due to inner ear diseases such as sudden hearing loss, perilymphatic fissura, labyrinthine concussion, and temporal bone fracture, and the like according to a cause thereof.

In one embodiment of the present invention, the hearing loss may be selected from the group consisting of noise-induced hearing loss, ototoxic hearing loss, hearing loss due to inner ear disease, and traumatic hearing loss.

The pharmaceutical composition of the present invention may be a composition for administration in the middle ear, inner ear, cochlea, vestibular organ, eustachian tube, or tympanic cavity, preferably a composition for administration in tympanic cavity.

The pharmaceutical composition according to the present invention may be formulated in a suitable form together with a pharmaceutically acceptable carrier, and may further include an excipient or diluent. The carrier includes all kinds of solvents, dispersion media, oil-in-water or water-in-oil emulsions, aqueous compositions, liposomes, microbeads and microsomes.

The pharmaceutically acceptable carrier may further include, for example, a carrier for oral administration or a carrier for parenteral administration. The carrier for oral administration may include lactose, starch, cellulose derivatives, magnesium stearate, stearic acid, and the like. In addition, various drug delivery materials used for oral administration may be included. In addition, the carrier for parenteral administration may include water, suitable oil, saline, aqueous glucose, glycol, and the like, and further include a stabilizer and a preservative. A suitable stabilizer includes antioxidants such as sodium hydrogen sulfite, sodium sulfite or ascorbic acid. A suitable preservative includes benzalkonium chloride, methyl- or propyl-paraben and chlorobutanol. The pharmaceutical composition of the present invention may further include a lubricant, a wetting agent, a sweetening agent, a flavoring agent, an emulsifying agent, a suspending agent, and the like in addition to the above ingredients. Other pharmaceutically acceptable carriers and formulations may refer to those known in the art.

The composition of the present invention may be administered to mammals comprising humans by any method. For example, the composition may be administered by a parenteral method. The parenteral administration method is not limited thereto, but may be intravenous, intramuscular, intraarterial, intramedullary, intrathecal, intracardiac, transdermal, subcutaneous, intraperitoneal, intranasal, enteral, topical, sublingual, rectal, intra-articular or intratympanic administration, and most preferably, intratympanic administration.

Intratympanic injection of the drug is a method of injecting the drug into the middle and/or inner ear behind the tympanic membrane.

In one embodiment of the present invention, the pharmaceutical composition of the present invention may be administered to the middle ear through transtympanic injection. In another embodiment, the pharmaceutical compositions of the present invention may be administered directly to the inner ear via non-transtympanic access to the inner ear.

In one embodiment of the present invention, the pharmaceutical composition may be administered through a syringe and a needle that passes through the tympanic membrane and directly approaches the round window membrane or ovoid window of the inner ear. The needle of the syringe is preferably used with a needle as small as possible to prevent the tympanic membrane perforation, and may be, for example, 22 gauge to 24 gauge.

The pharmaceutical composition of the present invention may be formulated as a formulation for oral administration or parenteral administration according to the route of administration as described above.

In the case of the formulation for oral administration, the composition of the present invention may be formulated as powders, granules, tablets, pills, sugar-coated tablets, capsules, liquids, gels, syrups, slurry, suspensions, etc. using methods known in the art. For example, the oral formulation may obtain tablets or sugar-coated tablets by mixing an active ingredient with a solid excipient, pulverizing the mixture, adding a suitable adjuvant, and then processing the mixture into a granular mixture. Examples of the suitable excipient may include sugars comprising lactose, dextrose, sucrose, sorbitol, mannitol, xylitol, erythritol and maltitol, starches comprising corn starch, wheat starch, rice starch and potato starch, celluloses comprising methyl cellulose, sodium carboxymethylcellulose and hydroxypropylmethylcellulose, fillers such as gelatin, polyvinylpyrrolidone, and the like. In addition, in some cases, cross-linked polyvinylpyrrolidone, agar, alginic acid or sodium alginate may be added as a disintegrant. In addition, the pharmaceutical composition may further include anti-coagulating agents, lubricants, wetting agents, flavorings, emulsifiers and antiseptics.

Formulations for parenteral administration may be formulated in the form of injections, creams, lotions, external ointments, oils, moisturizers, gels, aerosols and nasal inhalants by methods known in the art. These formulations are described in formulary commonly known in all pharmaceutical chemistry.

The total effective dose of the composition of the present invention may be administered to a patient in a single dose, or may be administered in a multiple dose for a long period of time according to a fractionated treatment protocol. In the pharmaceutical composition of the present invention, the content of the active ingredient may vary depending on the severity of disease. Preferably, the preferred total dose of the pharmaceutical composition of the present invention may be about 0.01 µg to 10,000 mg, most preferably 0.1 µg to 500 mg per 1 kg of patient's body weight per day. However, the dose of the pharmaceutical composition is determined by considering various factors comprising the age, body weight, health conditions, and gender of a patient, the severity of z disease, diet, and excretion rate, in addition to an administration route and the number of treatment times of the pharmaceutical composition. Considering such an aspect, those skilled in the art may determine a suitable effective dose of the composition of the present invention. The pharmaceutical composition according to the present invention is not particularly limited to the formulations, the administration routes, and the administration methods, as long as the effects of the present invention are shown.

In one embodiment of the present invention, the pharmaceutical composition may be administered before or after the onset of hearing loss or during the onset of hearing loss. The dosage may vary depending on an administration method, a duration of treatment, a condition of a patient to be treated, and the severity of hearing loss, and is determined by a physician in charge. The duration of treatment may be a range of about 1 hour to several days, weeks, or months, and may be a long period if necessary.

The term 'prevention' as used herein refers to a therapy that protects the onset of a disease or disorder so that the clinical symptoms of the disease do not develop. Thus, the 'prevention' refers to administering therapy (e.g., administering a therapeutic agent) to a subject before symptoms of the disease are detectable in the subject (e.g., administering a therapeutic material to a subject in the absence of a detectable infectious agent (e.g., virus) in the subject). The subject may be an individual at risk of developing a disease or disorder, such as an individual having one or more risk factors known to be associated with the development or onset of the disease or disorder.

In the present invention, the term 'treatment' refers to an approach for obtaining beneficial or desirable clinical results. For the purposes of the present invention, beneficial or desirable clinical results include non-limitedly palliation of symptoms, reduction of a disease range, stabilization (i.e., not worsening) of a disease condition, delay or reduced rate of disease progression, improvement or temporary palliation and reduction (which may be partial or total) of a disease condition, and whether it is detectable or undetectable. The 'treatment' refers to all therapeutic treatment and prophylactic or preventive measures. The treatments include the treatment required for disorders that have already occurred as well as disorders to be prevented. The 'palliating' of the disease means that the range of the disease condition and/or undesirable clinical symptoms are reduced or a time course of progression is delayed or lengthened, compared to no treatment.

Meanwhile, it will be apparent to those skilled in the art that the pharmaceutical composition of the present invention may further include a known material used for the treatment of hearing loss.

The present invention provides a method for preparing the drug-controlled release formulation comprising (a) encapsulating a steroidal anti-inflammatory agent in microspheres of hyaluronic acid or hyaluronic acid salt; (b) preparing an aqueous solution of hyaluronic acid or hyaluronic acid salt having a molecular weight of greater than 5,000,000 g/mol; and (c) dispersing the microspheres in the aqueous solution.

The present invention also provides the use of a steroidal anti-inflammatory agent encapsulated in microspheres of hyaluronic acid or hyaluronic acid salt to prepare a formulation for treating hearing loss, wherein the microspheres are dispersed in an aqueous solution of hyaluronic acid or hyaluronic acid salt having a molecular weight of greater than 5,000,000 g/mol.

The present invention also provides a method for treating hearing loss by administering an effective amount of a composition comprising a steroidal anti-inflammatory agent encapsulated in microspheres of hyaluronic acid or hyaluronic acid salt as an active ingredient to a subject in need thereof, wherein the microspheres are dispersed in an aqueous solution of hyaluronic acid or hyaluronic acid salt having a molecular weight of greater than 5,000,000 g/mol.

The 'effective dose' of the present invention means an amount which exhibits effects of improving, treating, detecting, and diagnosing the hearing loss, or inhibiting or reducing the hearing loss when administered to the subject. The 'subject' may be animals, preferably, mammals, particularly animals comprising humans and may also be cells, tissues, and organs derived from animals. The individual may be patients requiring the effects.

The 'treatment' of the present invention comprehensively refers to improving hearing loss or symptoms caused by the hearing loss, and may include treating or substantially preventing the disease, or improving the conditions thereof and includes palliating, treating or preventing a symptom or most of symptoms derived from the disease, but is not limited thereto.

The term "comprising" used herein is used in the same meaning as "including" or "characterized by", and does not exclude additional ingredients or steps of the method which are not specifically mentioned in the composition or the method according to the present invention. The term "consisting of" means excluding additional elements, steps or ingredients, etc., unless otherwise described. The term "essentially consisting of" means including materials or steps which do not substantially affect basic properties thereof in addition to the described materials or steps within the range of the composition or the method.

Advantageous Effects

According to the present invention, since the drug-controlled release formulation and the pharmaceutical composition for treating the hearing loss comprising the aqueous solution of ultra-high molecular hyaluronic acid as a drug carrier may exhibit a therapeutic effect for several weeks to several months with a single dose, it is possible to effectively treat diseases without repeated procedures without causing systemic side effects. In addition, since a chemical crosslinking agent for crosslinking hyaluronic acid is not used in the drug-controlled release formulation of the present invention, the risk of side effects such as an inflammatory response is very low.

MODES FOR THE INVENTION

Figure 1:
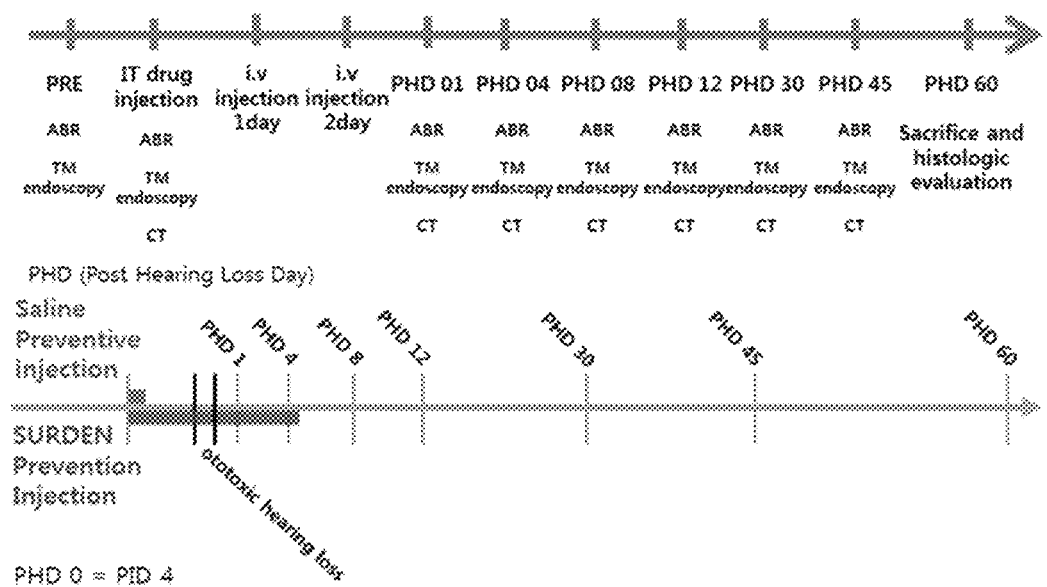
FIG. 1 is a diagram illustrating a test schedule for evaluating a hearing improvement test in a hearing loss-induced animal model.

Hereinafter, the present invention will be described in detail by the following Examples. However, the following Examples are just illustrative of the present invention, and the contents of the present invention are not limited to the following Examples.

Example 1: Preparation of Dexamethasone Microcapsules Using Ultra-Low Molecular Weight Hyaluronic Acid An aqueous solution containing 20% of ultra-low molecular weight hyaluronic acid with a molecular weight of less than 10,000 Da was prepared in ultrapure water, and 2.4% of dexamethasone disodium phosphate was completely dissolved therein.

The prepared hyaluronic acid-dexamethasone aqueous solution and a $CaCl_2$ (ionic compound containing $Ca^{2+}$) aqueous solution having a concentration of 10% were mixed at a ratio of 1:1 (v/v) to induce an ionic complex (precipitation) between the hyaluronic acid and $CaCl_2$. Thereafter, the precipitate was centrifuged at 12,000 rpm for 1 minute to remove a supernatant. In addition, in order to remove free ions that do not participate in the ionic complex, washing and centrifugation processes were performed three or more times using an excess of ultrapure water.

The ionic-complexed drug mixture was lyophilized to prepare dexamethasone encapsulated in ultra-low molecular weight hyaluronic acid.

Example 2: Preparation of Encapsulated Dexamethasone/Hyaluronic Acid Hydrogel Complex (SURDEN; Sustained Release Drug Encapsulation)

After preparing ultra-high molecular weight hyaluronic acid having adhesion, in-vivo stability in the tympanic cavity, and excellent biocompatibility as a carrier of the encapsulated dexamethasone, a microcapsule dexamethasone/hyaluronic acid complex was prepared using the ultra-high molecular weight hyaluronic acid.

The ultra-high molecular weight hyaluronic acid was prepared using a *Streptococcus* sp. UBC-U46 strain (Accession No.: KCTC13556BP) according to a production method specified in the prior patent (KR1020180130275).

The weight average molecular weight of the ultra-high molecular weight hyaluronic acid prepared according to the method was 7,000,000 g/mol.

The ultra-high molecular weight hyaluronic acid was dissolved in ultra-pure water to prepare an aqueous solution of ultra-high molecular weight hyaluronic acid having a concentration of 3%. Dexamethasone powder encapsulated in the ultra-low molecular weight hyaluronic acid prepared in Example 1 was added to the ultra-high molecular weight hyaluronic acid aqueous solution to a concentration of 1.5% and evenly mixed using a homogenizer to prepare a microcapsule dexamethasone/hyaluronic acid hydrogel complex (SURDEN) in which dexamethasone encapsulated in the ultra-low molecular weight hyaluronic acid was evenly mixed.

Example 3: Evaluation of Drug Carrier Retention Period and Drug Release Performance In order to evaluate the performance of the complex (SURDEN) prepared in Example 2 as a drug carrier, a hearing loss animal model was fabricated and the following experiment was performed.

(1) Fabrication of Hearing Loss Animal Model

To exclude a hormonal effect, experiments were performed using male SD rats. In order to induce ototoxic hearing loss, on the 4th day after IT vaccination, a combined drug of cisplatin (2 mg/kg), gentamycin (120 mg/kg), and furosemide (90 mg/kg) was injected into the tail jugular vein once daily for 2 days.

(2) Experimental Design

Dexamethasone (D) was applied to animals through two different methods using an intratympanic (IT) drug delivery method that delivered a drug through the tympanic membrane.

A first method was a treatment method used in existing hospitals, and a method of delivering the D at 12 mg/ml to a saline. A second method was a method of delivering the D at 12 mg/ml to the SURDEN prepared in Example 2 above. As a control, a hearing loss control group with no treatment was prepared. Each sample prepared as described above was administered by 0.04 ml per animal (each ear). A specific experimental schedule was illustrated in FIG. 1.

(3) Hearing Measurement

Hearing was measured at intervals of 1 to 14 days for about 2 months before and after induction of hearing loss. A auditory brainstem response (ABR) test was performed at a total of four frequencies of click, 8 kHz, 16 kHz, and 32 kHz to evaluate the characteristics of each frequency.

(4) Evaluation of Drug Carrier Retention Period

Figure 2:
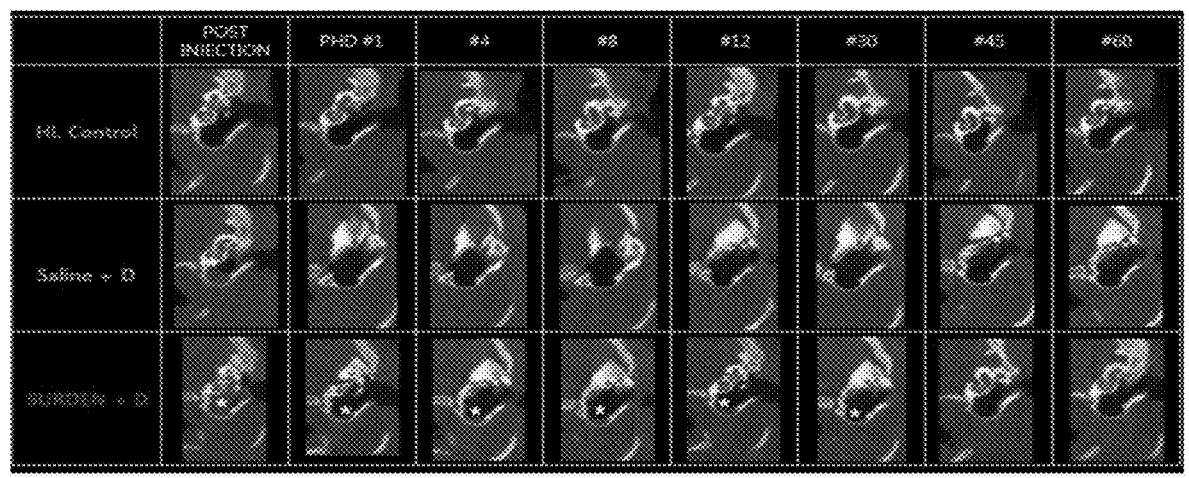
FIG. 2 is a result of evaluating a retention period of a drug/carrier in the tympanic cavity of the animal through CT scanning.

The retention period of the drug/carrier in the tympanic cavity of the animal confirmed at a CT scanning time indicated in the experimental schedule of FIG. 1 was 1.1±0.3 days in the case of saline+D and 41.1±27.0 days in the case of SURDEN. That is, it was confirmed that when SURDEN is used, the retention period of the drug/carrier may be extended about 40 times longer than that of the saline (FIG. 2).

(5) Safety Evaluation of Drug Carrier

Figure 3:
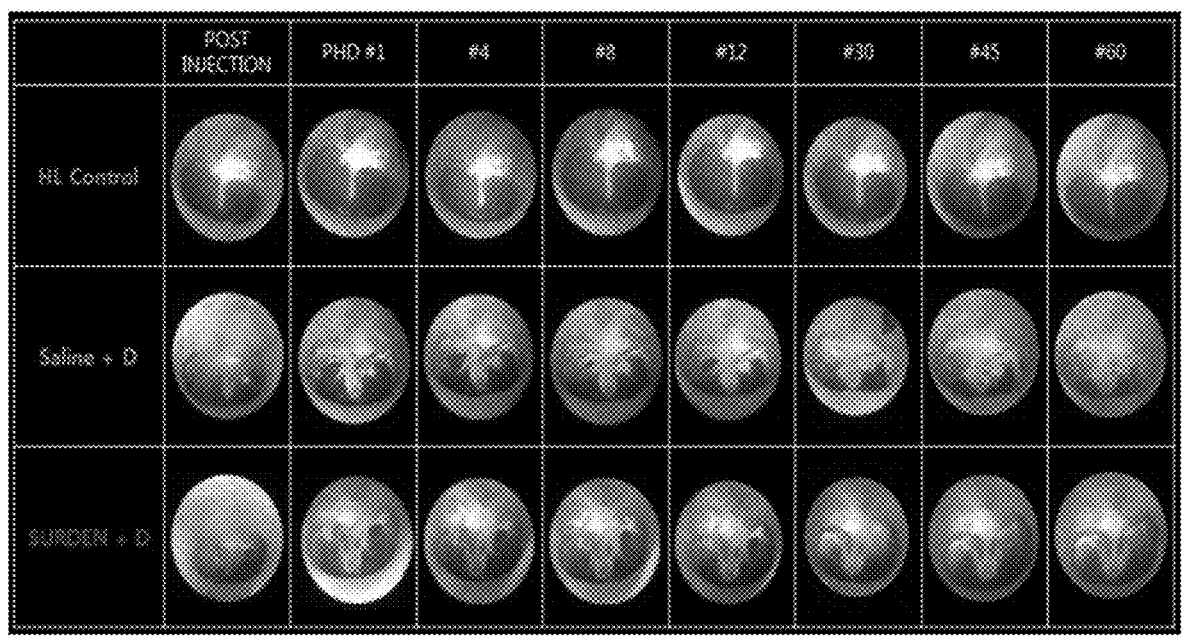
FIG. 3 is a diagram observing a process of recovering the tympanic membrane perforation that occurs during drug/carrier injection into the tympanic membrane over time.

As a result of regularly photographing a tympanic endoscope, the tympanic membrane perforation was completely blocked in a saline+D group after 21.6±12.6 days. In the case of a SERDEN+D group, the tympanic membrane perforation was completely blocked after 16.7±11.9 days. That is, when using SURDEN, since a period while the tympanic membrane perforation was healed was rather short or at least not long, it was confirmed that treatment was enabled without side effects (FIG. 3).

Figure 4:
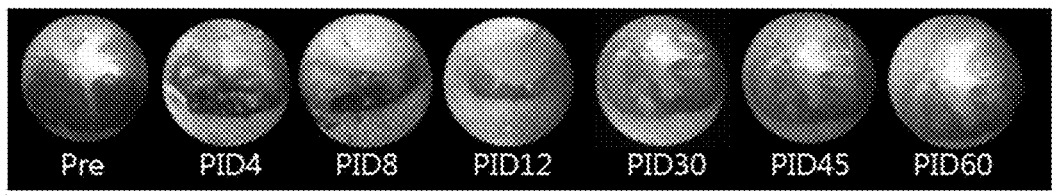
FIG. 4 is a diagram observing whether inflammation occurs in the tympanic membrane of an animal over time after administration of a drug/carrier (SUREDEN) according to the present invention.

In addition, as a result of observing the tympanic endoscope, no subjects developed middle ear inflammation due to SURSEN administration. Middle ear inflammation occurs when the drug/carrier was not biocompatible (FIG. 4), and in the case of the drug/carrier complex (SURDEN) of the present invention, since there was no inflammatory side effects, it was determined that drug/carrier complex (SURDEN) could be used successfully in the human body.

Example 4: Evaluation of Improved Hearing

In the case of SURDEN, from the first day (46.7 dB) when hearing loss was induced based on 32 kHz, the hearing began to be improved compared to saline+D (70.0 dB) or a control group (62.9 dB), and this tendency was well maintained to 4 days (46.7 dB), 8 days (52.5 dB), 12 days (47.5 dB), 21 days (46.7 dB), and 30 days (50.0 dB). When compared with the existing standard treatment method, saline+D, the treatment effect through SERDEN was superior by 23.3 dB to 26.7 dB. In general, considering that a clinically significant hearing difference was 15 dB, the treatment effect superior by 23.3 dB to 26.7 dB was a clinically significant difference.

This difference was also observed even at an intermediate frequency of 16 kHz. When compared with the existing standard treatment method, saline+D, the treatment effect of SERDEN was superior by 16.8 dB to 23.3 dB. Considering that a clinically significant hearing difference was 15 dB, the treatment effect superior by 16.8 dB to 23.3 dB at 16 kHz was a clinically significant difference.

Figure 5:
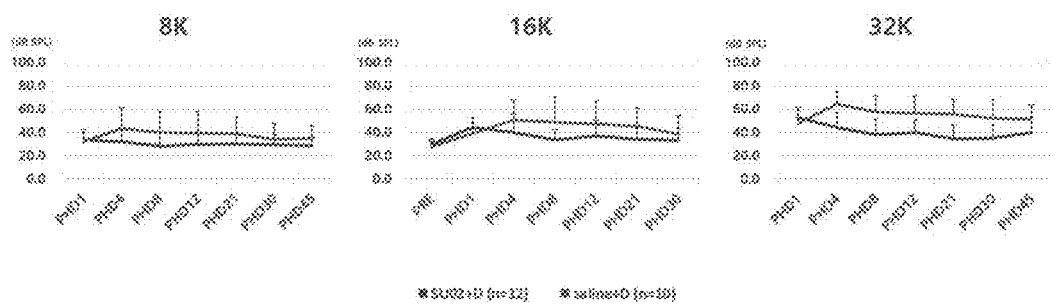
FIG. 5 is a result of evaluating a hearing improvement effect in an animal model of hearing loss (SU02+D: drug/carrier according to the present invention).

Even at the lowest frequency, 8 kHz, the treatment effect was the best in SURDEN. When compared with the existing standard treatment method, saline+D, the treatment effect through SERDEN was superior by 1.7 dB to 10.8 dB (FIG. 5).

As a result of synthesizing the results, it was confirmed that the hearing loss treatment effect of SURDEN was significantly superior to that of the existing standard treatment method, saline+D.

Example 5: Confirmation of Inflammatory Response

The present inventor compared whether the method according to the present invention induced an inflammatory response in the inner ear with a method disclosed in the prior registration patent (10-1877894).

Figure 6:
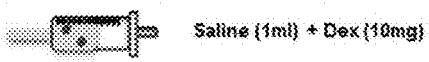
FIG. 6 is a schematic diagram illustrating a method of an experiment in which a drug/carrier of the prior art is injected into the tympanic membrane of an animal model of hearing loss.
Figure 6:
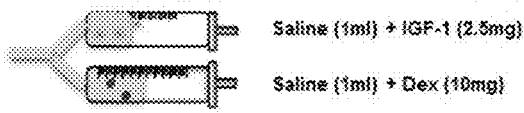
Figure 6:
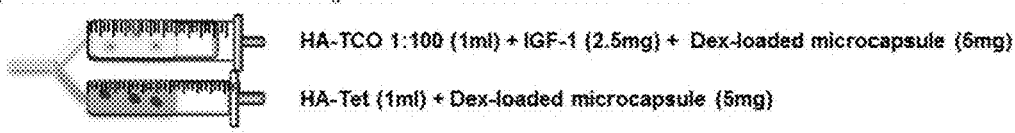

First, after induced hearing loss caused by noise in rats of normal hearing, the rats were divided into three groups ((1) dexamethasone+saline (D+saline), (2) Dexamethasone+ IGF-1+saline (D&G+saline), (3) dexamethasone-loaded LGA microcapsule+IGF-1+HA (cD&G+HA)) shown in FIG. 6 according to the method disclosed in the prior registration patent, and then each drug was injected into the tympanic membrane and a hearing test, a tympanic endoscope, and a CT scanning were performed up to 45 days.

In addition, a SURDEN-administered group according to the present invention was experimented in the same manner as above.

Figure 7:
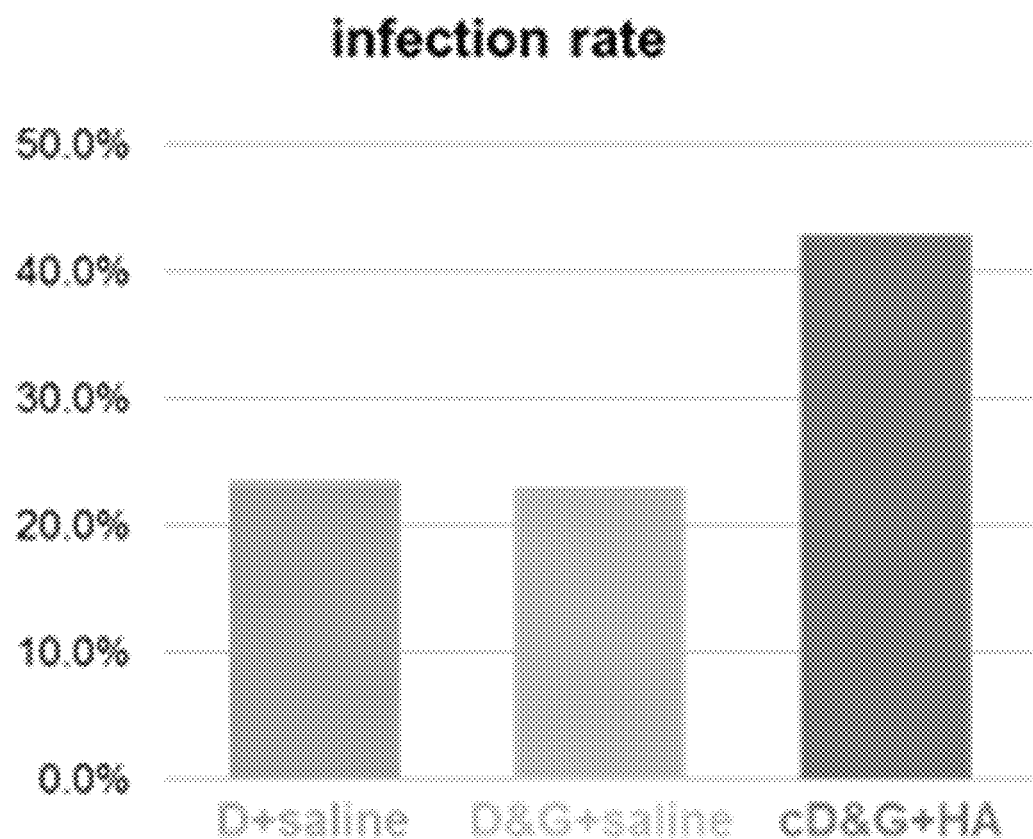
FIG. 7 is a result of evaluating a degree of inflammation after injecting the drug/carrier of the prior art into the tympanic membrane of the animal model of hearing loss.

The results thereof were illustrated in FIG. 7.

Figure 8:
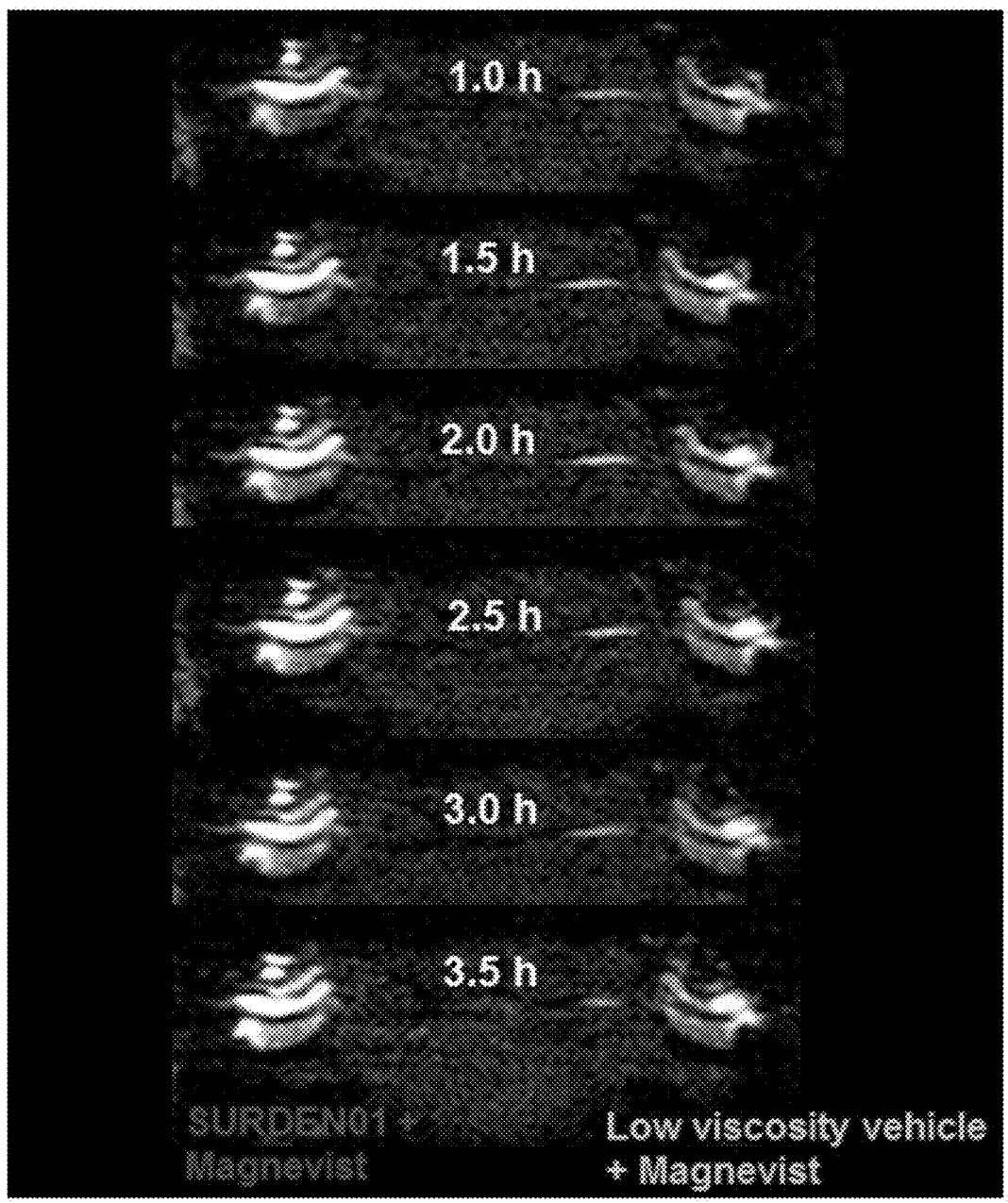
FIG. 8 is a diagram observing a contrast effect over time with 9.4T MRI after administering a carrier (SURDEN01+Magnevist) obtained by mixing a contrast agent with an aqueous solution of hyaluronic acid with a weight average molecular weight of 7,000,000 g/mol and a carrier (Low viscosity vehicle+magnevist) obtained by mixing a contrast agent with an aqueous solution of hyaluronic acid with a molecular weight of 1,000,000 to 3,000,000 g/mol into the tympanic membrane of rats.

As illustrated in FIG. 8, when a ratio for each group was calculated with respect to subjects causing an inflammatory response in the middle ear tissue after injecting the drug through the tympanic membrane, an inflammation rate in a Dexamethasone-loaded PLGA microcapsule+IGF-1+HA group was 42.3%, which was twice higher than that of other groups.

On the other hand, no inflammatory response was observed in the SURDEN-administered group (not illustrated in the results).

Example 6: Comparison of Controlled Release Ability and Hearing Loss Treatment Effect According to Molecular Weight of Hyaluronic Acid In order to comparatively evaluate a controlled release effect according to the molecular weight of the ultra-high molecular weight hyaluronic acid used in Example 2, controlled-release ability of a carrier using hyaluronic acid having a relatively lower molecular weight (1,000,000 to 3,000,000 g/mol) than a ultra-high molecular weight (weight average molecular weight of 7,000,000 g/mol) used to prepare the SURDEN in Example 2 was comparatively evaluated.

Specifically, a contrast agent was added to a hyaluronic acid aqueous solution (SURDEN) having a weight average molecular weight of 7,000,000 g/mol or a hyaluronic acid aqueous solution (Low viscosity vehicle) having a molecular weight of 1,000,000 to 3,000,000 g/mol, and each of these samples was injected into the tympanic membrane of rats, and then photographed using 9.4T MRI and quantitative analysis was performed.

Figure 9:
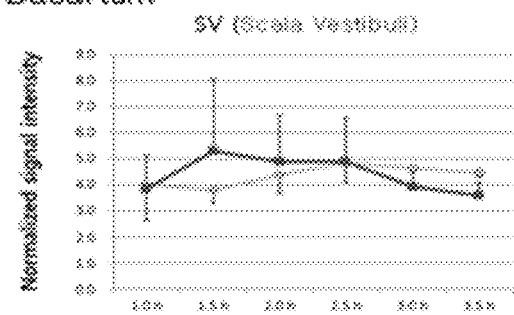
FIG. 9 is a diagram illustrating quantification of a contrast amount at each site in the rat tympanic membrane during the experimental process of FIG. 8 over time.
Figure 9:
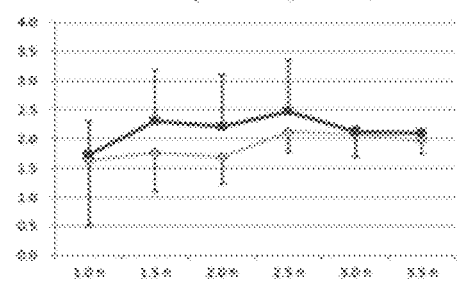
Figure 9:
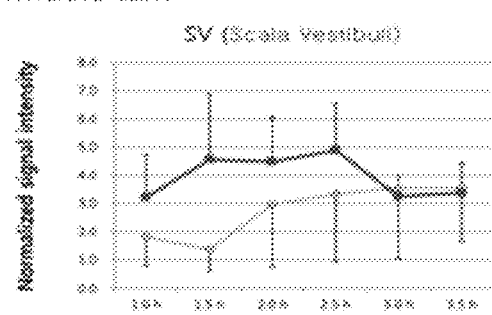
Figure 9:
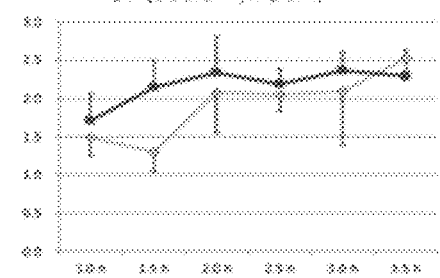
Figure 9:
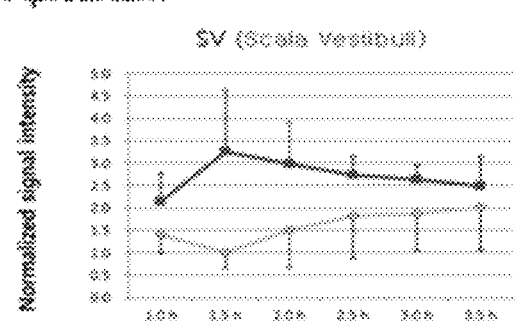
Figure 9:
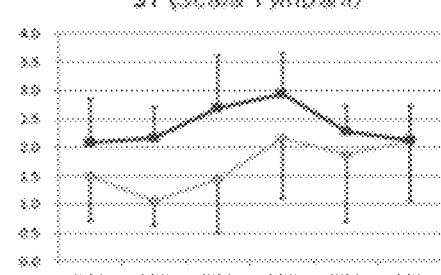

The results thereof were illustrated in FIGS. 9 and 10.

As shown in FIG. 9, it was confirmed that the contrast intensity was increased in the vestibular system and the tympanic system, and it was confirmed that the SURDEN-administered group showed a stronger synergistic effect than the low viscosity vehicle group at all time points and all areas.

In addition, as illustrated in FIG. 10, as a result of quantification, it was confirmed that the signal intensities of the SURDEN-administered group in the lower, middle, and upper layers of the cochlea were all higher than those of the low viscosity vehicle group.

In conclusion, in the case of the SURDEN, it was confirmed that the drug release ability was superior in the inner ear drug delivery by sustaining the drug at a higher concentration for a longer period of time and in a larger amount than a carrier using relatively low molecular weight hyaluronic acid.

INDUSTRIAL APPLICABILITY

According to the present invention, since the drug-controlled release formulation and the pharmaceutical composition for treating the hearing loss comprising the aqueous solution of ultra-high molecular hyaluronic acid as a drug carrier may exhibit a therapeutic effect for several weeks to several months with a single dose, it is possible to effectively treat diseases without repeated procedures without causing systemic side effects. In addition, since a chemical cross-linking agent for crosslinking hyaluronic acid is not used in the drug-controlled release formulation of the present invention, the risk of side effects such as an inflammatory response is very low and thus there is very high industrial applicability.

What is claimed is:
1. A drug-controlled release formulation in which a steroidal anti-inflammatory agent encapsulated in microspheres of hyaluronic acid or hyaluronic acid salt is dispersed in an aqueous solution of hyaluronic acid or hyaluronic acid salt having a molecular weight of greater than 5,000,000 g/mol, and wherein the hyaluronic acid or hyaluronic acid salt is not crosslinked.

2. The drug-controlled release formulation of claim 1, wherein the hyaluronic acid forming the microspheres has a molecular weight of 100,000 g/mol or less.

3. The drug-controlled release formulation of claim 1, wherein the steroidal anti-inflammatory agent is dexamethasone, prednisolone, methylprednisolone, betamethasone, hydrocortisone, or a combination thereof.

4. The drug-controlled release formulation of claim 1, wherein the hyaluronic acid having the molecular weight of greater than 5,000,000 g/mol is produced by a *Streptococcus* sp. UBC-U46 (Accession No. KCTC13556BP) strain.

5. The drug-controlled release formulation of claim 1, wherein the drug-controlled release formulation releases the steroidal anti-inflammatory agent at a target site for 20 days or longer.

6. The drug-controlled release formulation of claim 1, wherein the aqueous solution of hyaluronic acid or hyaluronic acid salt is an aqueous solution of 1 to 10% (w/v).

7. The drug-controlled release formulation of claim 1, wherein the formulation is a formulation for administration into middle ear, inner ear, cochlea, vestibular organ, eustachian tube, or tympanic cavity.

8. A pharmaceutical composition for preventing or treating hearing loss comprising a steroidal anti-inflammatory agent encapsulated in microspheres of hyaluronic acid or hyaluronic acid salt as an active ingredient, wherein the microspheres are dispersed in an aqueous solution of hyaluronic acid or hyaluronic acid salt having a molecular weight of greater than 5,000,000 g/mol, and wherein the hyaluronic acid or hyaluronic acid salt is not crosslinked.

9. The pharmaceutical composition of claim 8, wherein the pharmaceutical composition is injected into middle ear, inner ear, cochlea, vestibular organ, eustachian tube, or tympanic cavity.

10. The pharmaceutical composition of claim 8, wherein the hearing loss is selected from the group consisting of noise-induced hearing loss, ototoxic hearing loss, hearing loss due to inner ear disease, and traumatic hearing loss.

11. A method for preparing a drug-controlled release formulation, comprising the steps of: (a) encapsulating a steroidal anti-inflammatory agent in microspheres of hyaluronic acid or hyaluronic acid salt; (b) preparing an aqueous solution of hyaluronic acid or hyaluronic acid salt having a molecular weight of greater than 5,000,000 g/mol; and (c) dispersing the microspheres in the aqueous solution, and wherein the hyaluronic acid or hyaluronic acid salt is not crosslinked.

12. A method for treating hearing loss by administering an effective amount of a composition comprising a steroidal anti-inflammatory agent encapsulated in microspheres of hyaluronic acid or hyaluronic acid salt as an active ingredient to a subject in need thereof, wherein the microspheres are dispersed in an aqueous solution of hyaluronic acid or hyaluronic acid salt having a molecular weight of greater than 5,000,000 g/mol, and wherein the hyaluronic acid or hyaluronic acid salt is not crosslinked.

13. The method of claim 11, wherein the hyaluronic acid forming the microspheres has a molecular weight of 100,000 g/mol or less.

14. The method of claim 12, wherein the hyaluronic acid forming the microspheres has a molecular weight of 100,000 g/mol or less.

15. The method of claim 12, wherein the hyaluronic acid having the molecular weight of greater than 5,000,000 g/mol is produced by a *Streptococcus* sp. UBC-U46 (Accession No. KCTC13556BP) strain.

16. The method of claim 12, wherein the drug-controlled release formulation releases the steroidal anti-inflammatory agent at a target site for 20 days or longer.

17. The method of claim 12, wherein the aqueous solution of hyaluronic acid or hyaluronic acid salt is an aqueous solution of 1 to 10% (w/v).

18. The method of claim 12, wherein the formulation is a formulation for administration into middle ear, inner ear, cochlea, vestibular organ, eustachian tube, or tympanic cavity.

19. The method of claim 12, wherein the hyaluronic acid forming the microspheres has a molecular weight of 100,000 g/mol or less.

* * * * *